United States Patent [19]

Bönnemann

[11] Patent Number: 4,588,815

[45] Date of Patent: May 13, 1986

[54] METHOD FOR MANUFACTURING PYRIDINE AND PYRIDINE DERIVATIVES FROM ALKYNES AND CYANO COMPOUNDS IN THE PRESENCE OF COMPLEX COBALT OR RHODIUM COMPOUNDS WITH LIGANDS CONTAINING BORON

[75] Inventor: Helmut Bönnemann, Essen, Fed. Rep. of Germany

[73] Assignee: Studiengesellschaft Kohle mbH, Mulheim an der Ruhr, Fed. Rep. of Germany

[21] Appl. No.: 587,349

[22] Filed: Mar. 8, 1984

Related U.S. Application Data

[63] Continuation of Ser. No. 371,872, Apr. 26, 1982, abandoned.

[30] Foreign Application Priority Data

May 2, 1981 [DE] Fed. Rep. of Germany ....... 3117363

[51] Int. Cl.[4] .......................................... C07D 213/12
[52] U.S. Cl. .................................. 546/250; 546/251; 546/304
[58] Field of Search ............................... 546/250, 251

[56] References Cited

U.S. PATENT DOCUMENTS 4,006,149 2/1977 Bonnemann ...................... 546/250

OTHER PUBLICATIONS

Bonnemann et al., *Chem. Abstracts,* vol. 81, No. 19, Abst. No. 120,396c, Nov. 11, 1974.
Clement, *Chem. Abstracts,* vol. 81, No. 21, Abst. No. 135,962h, Nov. 25, 1974.
Bonnemann et al., *Chem. Abstracts,* vol. 84, No. 5, Abst. No. 30,909e, Feb. 2, 1976.
Bonnemann et al., *Chem. Abstracts,* vol. 93, No. 9, Abst. No. 95,136f, Sep. 1, 1980.
Yasuo et al., *Chem. Abstracts,* vol. 85, No. 5, Abst. No. 32,779g, Aug. 2, 1976.

*Primary Examiner*—Alan L. Rotman
*Attorney, Agent, or Firm*—Sprung, Horn, Kramer & Woods

[57] ABSTRACT

The preparation of pyridine and pyridine derivatives from alkynes and cyano compounds including HCN is disclosed. The process can be carried out in the presence of a cobalt or rhodium catalyst having at least one ligand with one or more boron atoms. Certain new cobalt or rhodium catalysts containing such ligand are also disclosed. Also disclosed is a process for the formation of 2-aminopyridine by contacting acetylene with cyanamide such as in the presence of a cobalt or rhodium catalyst which has at least one ligand with one or more boron atoms.

36 Claims, No Drawings

METHOD FOR MANUFACTURING PYRIDINE AND PYRIDINE DERIVATIVES FROM ALKYNES AND CYANO COMPOUNDS IN THE PRESENCE OF COMPLEX COBALT OR RHODIUM COMPOUNDS WITH LIGANDS CONTAINING BORON

This is a continuation of application Ser. No. 371,872, filed Apr. 26, 1982, now abandoned.

BACKGROUND OF THE INVENTION

1. Field of the Invention

The invention is a catalytic method for manufacturing singly or multiply substituted pyridine derivatives from alkynes and nitriles and unsubstituted pyridine from acetylene and hydrogen cyanide.

2. Discussion of Prior Art

The methods for manufacturing pryidine derivatives known up to the present time employ cobalt catalysts in which the metal atom is complexly bonded to pure hydrocarbon ligands of, for example, the allyl or cyclopentadienyl type (DBP 2 416 295, Studiengesellschaft Kohle mbH; corresponding to U.S. Pat. No. 4,006,149 whose disclosure is specifically incorporated herein by reference; DOS 2 615 309, Lonza AG; H. Yamazaki & Y. Wakatsuki, *Synthesis*, 1976, p. 26). These methods are economically unsatisfactory because of the exhaustion of the catalyst. DBP 2 840 460 specifies a method for the selective manufacture of the polymerization-sensitive 2-vinylpyridine that, subject to certain conditions, allows a much more economical utilization of the same type of catalyst to obtain up to 300 mol of pyridine derivative per gram atom of cobalt. Admittedly, this method can not avoid the employment of large amounts of foreign solvents, which make the product more difficult to process.

A catalytic process that allows the manufacture of unsubstituted pyridine from acetylene and hydrogen cyanide is not known as the present time. Although W. Ramsay was, of course, successful as early as 1876 in obtaining small amounts of pyridine from HCN and acetylene in the gaseous phase at 800° C. in a red-hot iron tube (W. Ramsay, *Philos. Mag.*, 5, 2, 271 [1876]), this uncatalyzed reaction turned out later to be hard to reproduce (R. Meyer & A. Tanzen, *Chem. Ber.*, 46, 3186 [1913]) and is economically impractical.

SUMMARY OF INVENTION

It has surprisingly now been discovered that penetration complexes of cobalt or rhodium with ligands that contain one or two boron atoms are highly effective catalysts for the manufacture of pyridines and pyridine derivatives from alkynes and cyano compounds. These novel cobalt catalysts can be employed first of all to drastically increase the catalytic activity and thus radically improve catalyst exploitation under mild reaction conditions.

This new type of catalyst permits a five-fold improvement over state-of-the-art cobalt exploitation in the synthesis of 2-vinylpyridine from acetylene and acrylonitrile and eliminates the need for foreign solvents without detriment to the product yields as a result of polymerization, for instance. Generally, nitriles can be economically and practically converted with boron-modified cobalt catalysts into 2-substituted pyridines, whereas nitriles with substituted alkynes can be catalytically converted into collidine derivatives. This method also allows for the first time the catalytic mix-cyclization of acetylene with hydrogen cyanide into unsubstituted pyridine under mild conditions.

Suitable ligands are usually organic boron compounds that can, with transition metals, especially cobalt and rhodium, form penetration complexes. These compounds include borabenzene derivatives, borols, and borepines, as well as compounds that contain several boron atoms, such as diborolene derivatives.

The method in accordance with the invention can be carried out with cobalt complexes with appropriate ligands containing boron that have been previously prepared in accordance with known methods (G. E. Herberich & G. Geiss, *Chem.Ber.*, 105, 3413–23 [1972] and G. E. Herberich, W. Koch, & H. Lueken, *J. Organomet. Chem.*, 160, 17–23 [1978], for example). It is, however, especially practical to convert free boron ligands with organocobalt compounds such as cyclooctenylcobalt cyclooctadiene, methylheptadienylcobalt butadiene, or trisallylcobalt into hightly active catalyst in situ.

The reaction can be effected at various temperatures over a wide range but preferably from 70° to 140° C., although a range of 50° to 180° C. can also be employed. The reaction generally takes from 30 to 300 minutes, although the time can be significantly decreased or increased by the use of appropriate reaction apparatus such as flow tubes. It is practical to employ pressures reanging from 8 to 45 bars, preferably from 20 to 40 bars, for the catalytic conversion of cyano compounds with acetylene.

The method in accordance with the invention can be carried out either discontinuously or continuously. Although it is not necessary to add foreign solvents, it is possible to do so if desirable for practical reasons.

The pyridine derivatives 2-picoline and 2-vinylpyridine manufactured in accordance with the invention are of significance for the manufacture of terpolymer bonding agents in the automobile-tire industry, collidine derivatives are valuable special-purpose solvents, and unsubtituted pyridine is a starting material in many technical synthesis, in the manufacture of herbicides for instance.

DESCRIPTION OF SPECIFIC EMBODIMENTS

While the invention has been described above and in the ensuing examples largely in terms of using acetylene as the alkyne, monoalkyl and/or monoaryl substituted derivatives of acetylene are also useful, as are di-substituted acetylenes such as butyne-(2) tolane or, for example, propargyl methyl ether can also be used. It is also contemplated to carry out the reaction with two different acetylene derivatives such a co-cyclo addition. For example, the joint reaction of acetylene, propyne and acetonitrile can be performed to give mixed lutidine derivatives in addition to α-picoline and isomeric collidines.

Examples of suitable cyano compounds which may be used include cyanic acid and derivatives thereof such as cyanamide and further alkyl-, aryl-, aralkyl- and alkenyl-nitrile-derivatives or dinitriles such as malanodinitrile or adipo-nitrile, as well as terephthalic acid dinitrile.

Alkyl radicals contemplated herein are those containing 1 to 18 carbon atoms, preferably 1 to 8 carbon atoms. Aryl moieties contemplated herein include those having up to 18 carbocyclic carbon atoms, preferably 6 to 12 carbocyclic carbon atoms. Aryl alkyl moieties contemplated herein include those having up to 18 carbocyclic carbon atoms and up to 8 carbon atoms in the alkyl chain. Alkenyl moieties include those having 2 to 18 carbon atoms in the chain, preferably 2 to 8 carbon atoms in the chain.

The process according to the invention is preferably carried out in the presence of the nitrile as solvent (if necessary or desired in the presence of a diluent) at temperatures broadly in the range between −10° C. and 150° C. and preferably 50° to 100° C. under pressure conditions under which the reactants are completely or partially maintained in liquid state. In general, the pressures are not in excess of 30 atmospheres. The acetylenes charged are reacted substantially quantitatively. Excess nitrile can be recovered by distillation.

Suitable diluents for the process include paraffin hydrocarbons, aromatics, ethers, pure or water-containing alcohols and halo hydrocarbons. The catalysts can be generated in situ or pre-prepared and be introduced during the progress of the reaction or they can be introduced in the form of a solution of the nitrile reactant to which the alkyne can thereafter be added. The process can be performed batch-wise or in a continuous-flow-reactor.

EXAMPLE 1

0.102 g (0.3188 mmol) of 1-phenylborinatocobalt cycloocta-(1,5)-diene is dissolved in 124.7 g (2.353 mol) of acrylonitrile. This solution is siphoned at room temperature into a 500-ml stainless-steel autoclave with an interior cooling coil. The acrylonitrile is saturated at 26.5 bars with approximately 34 g (1.31 mol) of acetylene. The solution is heated for 12 minutes to 105° C. while the pressure in the autoclave is allowed to rise to a maximum of 37 bars at 90° C. The reaction is allowed to continue for 240 minutes, after which the autoclave is inwardly cooled with water to 20° C. in 8 minutes.

144.7 g of the crude product are withdrawn from the autoclave and the volatile components condensed off at 0.2 Torr, leaving a residue of 0.6 g.

Gas-chromatography shows that the 143.4 g of condensate contain 104.8 g (1.978 mol) of acrylonitrile and 32.4 g (0.308 mol) of 2-vinylpyridine, corresponding to a 23% solution of vinylpyridine in acrylnitrile. The yield in terms of acrylonitrile converted is 82.1%. Catalyst utilization is 966 mol of pyridine derivative/gram atom of cobalt.

EXAMPLE 2

The procedure described in Example 1 is followed.
Ingredients:
  0.0708 g (0.2212 mmol) 1-phenylborinatocobalt cycloocta-(1,5)-diene,
  128.0 g (2.415 mol)acrylonitrile
  appr. 34.3 g (1.32 mol)acetylene.
Reaction conditions:
  Temperature: 111° C.
  Time: 120 minutes
Discharge: 144.6 g
Condensate: 144.0 g
Residue: 0.4 g
Gas-chromatography results:
  Acrylonitrile: 112.1 g (2.115 mol)
  2-vinylpyridine: 27.4 g (0.261 mol) 19% sol. in acrylonitrile
  Yield in terms of acrylonitrile converted: 87.0%
  Amount of catalyst employed: 1180 mol of pyridine derivative/g-atom of cobalt.

EXAMPLE 3

The procedure described in Example 1 is followed.
Ingredients:
  0.018 g (0.0563 mmol) 1-phenylborinatocobalt cycloocta-(1,5)-diene
  127.3 g (2.402 mol)acrylonitrile
  appr. 34.3 g (1.32 mol)acetylene.
Reaction conditions:
  Temperature: 106° C.
  Time: 120 minutes
Discharge: 132.4 g
Condensate: 132.0 g
Residue: 0.05 g
Gas-chromatography results:
  acrylonitrile 121.7 g (2.296 mol)
  2-vinylpyridine: 8.9 g (0.085 mol)
  Yield in terms of acrylonitrile converted: 80.2%
  Amount of catalyst employed: 1510 mol of pyridine derivative/g-atom of cobalt.

EXAMPLE 4

The procedure described in Example 1 is followed.
Ingredients:
  0.0545 g (0.1703 mmol) 1-phenylborinatocobalt cycloocta-(1,5)-diene
  131.1 g (2.474 mol)acrylonitrile
  appr. 34.5 g (1.33 mol)acetylene.
Reaction conditions:
  Temperature: 111° C.
  Time: 120 minutes
Discharge: 146.4 g
Condensate: 145.8 g
Residue: 0.5 g
Gas-chromatography results:
  Acrylonitrile: 114.5 g (2.160 mol)
  2-vinylpyridine: 26.1 g (0.249 mol)
  Yield in terms of acrylonitrile converted: 79.5%
  Amount of catalyst employed: 1462 mol of pyridine derivative/g-atom of cobalt.

EXAMPLE 5

0.0514 g (0.1601 mmol) of 1-phenylborinatocobalt cycloocta-(1,5)-diene is dissolved in 116.8 g (2.849 mol) of acetonitrile. This solution is siphoned at room temperature into a 500-ml stainless-steel autoclave with an interior cooling coil. The acrylonitrile is saturated at 14.5 bars with approximately 25.0 g (0.96 mol) of acetylene. The solution is heated for 10 minutes to 105° C. while the pressure in the autoclave is allowed to rise to a maximum of 26 bars. The reaction is allowed to continue for 90 minutes at 110° C., after which the autoclave is inwardly cooled with water to room temperature in 6 minutes. 123.1 g of the crude product are withdrawn from the autoclave and the volatile components condensed off at 0.2 torrs, leaving a residue of 0.1 g.

Gas-chromatography shows that the 122.9 g of condensate contain 112.6 g (2.746 mol) of acetonitrile and 9.4 g (0.101 mol) of α-picoline.

The yield in terms of acetonitrile converted is 98%. Catalyst utilization is 629 mol of pyridine derivative/gram atom of cobalt.

EXAMPLE 6

The procedure described in Example 5 is followed.
Ingredients:
  0.0223 g (0.06969 mmol) 1-phenylborinatocobalt cycloocta-(1,5)-diene 118.6 g (2.893 mol)acetonitrile
appr. 24.4 g (0.94 mol)acetylene.
Reaction conditions:
   Temperature: 110° C.
   Time: 99 minutes
Discharge: 123.2 g
Condensate: 123.0 g
Residue: 0.1 g
Gas-chromatography results:
   Acetonitrile: 115.4 g (2.814 mol)
   α-picoline: 7.1 g (0.0763 mol)
   Yield in terms of acetonitrile converted: 97.5%
   Amount of catalyst employed: 1095 mol of pyridine derivative/g-atom of cobalt.

EXAMPLE 7

0.350 g (1.094 mmol) of 1-phenylborinatocobalt cycloocta-(1,5)-diene is dissolved in 260 ml of benzene and treated with 30 ml (0.737 mol) of HCN. The resulting solution is siphoned at room temperature into a 500-ml stainless-steel autoclave with a magnetic stirrer. The solution is saturated at 6.5 bars with approximately 15.2 g (0.58 mol) of acetylene. The solution is heated for 18 minutes to a reaction temperature of 110° C. Maximum pressure was 23 bars. The reaction is allowed to continue for 60 minutes, after which the autoclave is inwardly cooled to room temperature. Unreacted HCN and acetylene were pumped off at room temperature over an FeSO4 solution.

239.7 g of the crude product are withdrawn from the autoclave and the volatile components condensed off at 0.2 torrs, leaving a residue of 0.4 g.

Gas-chromatography shows that the 239.1 g of condensate contain 8.86 g of pyridine.

The yield in terms of HCN employed is 15.2%. Catalyst utilization is 103 mol of pyridine/gram atom of cobalt.

EXAMPLE 8

0.055 g (0.1719 mmol) of 1-phenylborinatocobalt cycloocta-(1,5)-diene is dissolved in 250 ml (195.5 g=3.554 mol) of propionitrile. This solution is siphoned at room temperature into a 500-ml stainless-steel autoclave with a magnetic stirrer. 35.6 g (0.89 mol) of propyne was also added under pressure. The solution is heated for 13 minutes to a reaction temperature of 114° C. The reaction is allowed to continue for 112 minutes, after which the autoclave is inwardly cooled to room temperature.

229.6 g of the crude product are withdrawn from the autoclave and the volatile components condensed off at 0.2 Torr, leaving a residue of 0.2 g.

Gas-chromatography shows that the 228.9 g of condensate contain 187.2 g (3.404 mol) of propionitrile and 8.14 g (0.148 mol) of dimethyl-2-ethyl pyridine. The yield in terms of propionitrile converted is 98.7%. Catalyst utilization is 861 mol of pyridien derivative/gram atom of cobalt.

EXAMPLE 9

The procedure described in Example 1 is followed, but with 1-phenylborinatocobalt norbornadiene as a catalyst.
Ingredients:
   0.0408 g (0.1342 mmol) 1-phenylborniatocobalt norbornadiene
   126.6 g (2.389 mol)acrylonitrile
   33.7 g (1.30 mol)acetylene.

Reaction conditions:
   Temperature: 105° C.
   Time: 114 minutes
Discharge: 137.8 g
Condensate: 137.2 g
Residue: 0.2 g
Gas-chromatography results:
   Acrylonitrile: 114.1 g (2.153 mol)
   2-vinylpyridine: 18.25 g (0.174 mol)
   Yield in terms of acrylonitrile converted: 73.7%
   Amount of catalyst employed: 1297 mol of pyridine derivative/g-atom of cobalt.

EXAMPLE 10

0.1545 g (0.436 mmol) of bis-1-phenylborinatocobalt is dissolved in 250 ml (193.7 g=4.724 mol) of acetonitrile. This solution is siphoned at room temperature into a 500-ml stainless-steel autoclave with a magnetic stirrer. The solution is saturated at 5 bars with approximately 7.5 g (0.29 mol) of acetylene. The solution is heated for 17 minutes to a reaction temperature of 161° C. at a maximum pressure of 18.2 bars. The reaction is allowed to continue for 47 minutes, after which the autoclave is inwardly cooled to room temperature.

197.5 g of the crude product are withdrawn from the autoclave and the volatile components condensed off at 0.2 Torr, leaving a residue of 0.2 g.

Gas-chromatography shows that the 197.2 g of condensate contain 190.9 g (4.656 mol) of acetonitrile and 6.2 g (0.0667 mol) of α-picoline. The yield in terms of acetonitrile converted is 97.5%%. Catalyst utilization is 153 mol of pyridine derivative/gram atom of cobalt.

EXAMPLE 11

2.78 g (12.5 mmol) of methylheptadienylcobalt butadiene is dissolved in 96 ml of pentane along with 1.92 g (12.5 mmol) of 1-phenyl-1,4-dihydroborabenzene at −30° C. The reaction solution is brought slowly to room temperature and allowed to continue reacting for 20 hours. 1.35 g (12.5 mmol) of cycloocta-(1,5)-diene is added an the solution reflux heated for approximately 24 hours. The mixture is cooled to room temperature and 1 ml (0.125 g-atoms of cobalt) of it treated with a catalyst solution of 125.8 g (2.374 mol) of acrylnitrile. The solution is siphoned at room temperature into a 500-ml stainless-steel autoclave with a magnetic stirrer. The solution is saturated at 16 bars with approximately 33.7 g (1.30 mol) of acetylene. The remaining procedure follows Example 1.
Reaction conditions:
   Temperature: 105° C.
   Time: 80 minutes
Discharge: 133.2 g
Condensate 132.8 g
Residue 0.2 g
Gas-chromatography results:
   Acrylonitrile: 115.6 g (2.182 mol)
   2-Vinylpyridine: 14.0 g (0.133 mol)
   Yield in terms of acrylonitrile converted: 69.1%
   Amount of catalyst employed: 1064 mol of pyridine derivative/g-atom of cobalt.

EXAMPLE 12

0.190 g (1 mmol) of 1,3,4,5-tetraethyl-2-methyl-1,3-diborolene and 0.276 g (1 mmol) of π-cyclooctenyl-cobalt cycloocta-(1,5)-diene are dissolved in 3 ml of toluene. The solution is heated to 60° C. over 1 hour, during which a slight reddish discoloration was observed. After reaction the solvent was extracted and the residue washed with 5 ml of cold pentane.

Crystallization at −80° C. yielded 0.294 g (0.826 mmol) of 1,3,4,5-tetraethyl-2-methyl-1,3-diborolenyl-cobalt cycloocta-(1,5)-diene. The yield was 82.6%

Ultimate analysis: Theor: Co 16.6%, B 6.1%, C 67.5%, H 9.8%. Emp.: Co 16.9%, B 6.0%, C 67.2%, H 9.9%.

0.121 g (0.340 mmol) of the catalyst prepared in this way are dissolved in 123.35 g (2.327 mol) of acrylnitrile and converted with acetylene as described in Example 1.

Reaction conditions:
Temperature: 111° C.
Time: 135 minutes
Discharge: 129.0 g
Condensate: 128.8 g
Residue: 0.2 g
Gas-chromatography results:
Acrylnitrile: 116.87 g (2.205 mol)
2-vinylpyridien: 8.73 g (0.0831 mol)
Yield in terms of acrylnitrile converted: 68.1%
Amount of catalyst employed: 244 mol of pyridine derivative/g-atom of cobalt.

EXAMPLE 13

1,3,4,5-Tetraethyl-2-methyl-1,3-diborolenylcobalt cycloocta-(1,5)-diene cycloocta-(1,5)-diene is prepared as described in Example 12. Part of it is employed as a catalyst.

Ingredients:
0.255 g (0.7168 mmol) 1,3,4,5-tetraethyl-2-methyl-1,3-diborolenyl-cobalt
123.3 g (2.326 mol) acrylonitrile Reaction conditions:
Temperature: 83° C.
Time: 242 minutes
Discharge: 135.2 g
Condensate: 134.1 g
Residue: 0.4 g
Gas-chromatography results:
Acrylonitrile: 108.65 g (2.050 mol)
2-Vinylpyridine: 20.21 g (0.192 mol)
Yield in terms of acrylonitrile converted: 69.6%
Amount of catalyst employed: 268 mol of pyridine derivative/g-atom of cobalt.

EXAMPLE 14

0.190 g (mmol) of 1,3,4,5-tetraethyl-2-methyl-1,3-diborolene and 0.280 g (1.014 mmol) of $\pi$-cyclooctenyl-cobalt cycloocta-(1,5)-diene are dissolved in 4 ml (3.56 g) of toluene. The solution is heated over 1 hour to 60° C. After it is cooled to room temperature, 127.1 g (2.398 mol) of acrylonitrile added.

This solution is siphoned at room temperature into a 500-ml stainless-steel autoclave with a magnetic stirrer. The solution is saturated at 15 bars with approximately 35.8 g (1.38 mol) of acetylene. The solution is heated for 21 minutes to 110° C., resulting in a maximum pressure of 43.8 bars. The reaction is allowed to continue for 230 minutes, after which the autoclave is inwardly cooled to room temperature in 17 minutes.

147.7 g of the crude product are withdrawn from the autoclave and the volatile components condensed off at 0.2 Torr, leaving a residue of 0.5 g.

Gas-chromatography shows that the 146.9 g of condensate contain 105.7 g (1.994 mol) of acrylonitrile and 30.2 g (0.288 mol) of 2-vinylpyridine. The yield in terms of acrylonitrile converted is 71.3%. Catalyst utilization is 284 mol of pyridine derivative/gram atom of cobalt.

EXAMPLE 15

The procedure described in Example 1 is followed, but 1-phenylborinatorhodium cycloocta-(1,5)-diene is employed as a catalyst.

Ingredients:
0.063 g (0.173 mol) 1-phenylborinatorhodium cycloocta-(1,5)-diene
128.6 g (2.4237 mol) acrylonitrile
28 g (1.078 mol) acetylene Reaction conditions:
Temperature: 132° C.
Time: 142 minutes
Discharge: 130.5 g
Condensate: 130.1 g
Residue: 0.4 g
n Gas-chromatography results:
Acrylonitrile: 125.83 g (96.72%)
2-vinylpyridine: 3.23 g (2.48%)
Yield of 2-vinylpyridine in terms of acrylonitrile converted: 59.2%.
Amount of catalyst employed: 178 mol of pyridine derivative/g-atom of rhodium.

EXAMPLE 16

Catalyst: 1-phenylborinatocobalt cycloocta-(1,5)-diene.

A catalyst solution and a substrate solution are eductor pumped (at 20 and 40 ml/h respectively) into a stainless-steel continuous-throughflow stirring vessel with an effective capacity of 82 ml and external thermostating. The catalyst solution is 0.2 g (0.629 mmol) of 1-phenylborinatocobalt cycloocta-(1,5) -diene in 200 ml (147.7 g) of benzene, the substrate solution 139.7 g (2.636 mol) of acrylonitrile, 41.9 g of toluene, and 39.0 g of pyridine in 435 ml (380.1 g) of benzene into which 118.0 g (4.538 mol) of acetylene has been pressed.

The reactor is raised to a temperature of 92° C. over 45 minutes and maintained at that temperature until the outflow shows a concentration of 0.6% by weight of 2-vinylpyridine. The temperature is then raised to 124° C. over 110 minutes and the reactor allowed to become stationary. 0.085 g-atoms of cobalt were detected in the reactor in the stationary state. Gas chromatography showed 22.72 mmol (2.386 g) of 2-vinylpyridine with catalyst utilization of 267 mol of 2-vinylpyridine/g-atom of cobalt or 475.8 kg of 2-vinylpyridine/kg of cobalt. The stationary acrylonitrile conversion was thus 25.4 mmol (1.35 g), the yield of 2-vinylpyridine in terms of acrylnitrile converted 89.4%, and the molar ratio of 2-vinylpyridine to benzene 0.9:1.

EXAMPLE 17

Catalyst: 1-phenylborinatocobalt cycloocta-(1,5)-diene
0.0372 g (0.1160 mmol) of 1-phenylborinatocobalt cycloocta-(1,5)-diene is dissolved in 123.4 g (2.328 mol) of acrylonitrile. This solution is siphoned at room temperature into a 500-ml stainless-steel autoclave with an interior cooling coil. The acrylonitrile is saturated at 19 bars with approximately 55 g (2.115 mol) of acetylene. The solution is heated for 60 minutes to 120° C. while the pressure in the autoclave is allowed to rise to a maximum of 46 bars. The reaction is allowed to continue for 135 minutes, after which the autoclave is inwardly cooled with water to 20° C. in 25 minutes.

137.8 g of the crude product are withdrawn from the autoclave and the volatile components condensed off at $10^{-3}$ Torr leaving a residue of 0.9 g.

Gas-chromatography shows that the 136.9 g of condensate contain 107.7 g (2.032 mol) of acrylonitrile 23.09 g (0.220 mol) of 2-vinylpyridine, and 3.27 g (0.042 mol) of benzene, corresponding to a 17.7% solution of 2-vinylpyridine in acrylonitrile. The molar ratio of 2-vinylpyridine to benzene is thus 5.2:1 and the yield of 2-vinylpyridine in terms of acrylonitrile converted is 74.3%.

12.7% of the acrylonitrile has been converted and catalyst utilization is 1896 mol of 2-vinylpyridine/gram atom of cobalt or 3373.8 kg of 2-vinylpyridine/kg of cobalt.

EXAMPLE 18

Catalyst: 1-phenylborinatocobalt cycloocta-(1,5)-diene
32.3 g (0.1009 mmol) of 1-phenylborinatocobalt cycloocta-(1,5)-diene is dissolved in 125.7 g (2.372 mol) of acrylonitrile. This solution is siphoned at room temperature into a 500-ml stainless-steel autoclave with an interior cooling coil. The solution is saturated at 8 bars with acetylene. The solution is heated for 11 minutes to 85° C. while the pressure in the autoclave is allowed to rise to 16.5 bars. Acetylene is now pressed in until the solution is saturated with acetylene at 20 bars. Further heating over 18 minutes to 120° C. increases the pressure to 25 bars. A total of 27 g (1.038 mol) of acetylene is added. After 120 minutes of reaction the autoclave is inwardly cooled with water to 20° C. in 35 minutes.

129.1 g of the crude product are withdrawn from the autoclave and the volatile components condensed off at $10^{-3}$ Torr, leaving a residue 0.2 g.

Gas-chromatography shows that the 129.7 g of condensate contain 111.0 g (2.094 mol) of acrylonitrile, 15.17 g (0.145 mol) of 2-vinylpyridine, and 0.60 g (0.008 mol) of benzene, corresponding to a 12.0% solution of 2-vinylpyridine in acrylonitrile. The molar ration of 2-vinylpyridine to benzene is thus 18.1:1 and the yield of 2-vinylpyridine in terms of acrylonitrile converted is 52.2%.

11.7% of the acrylonitrile has been converted and catalyst utilization is 1432 mol of 2-vinlypyridine/gram atom of cobalt or 2548 kg of 2-vinylpyridine/kg of cobalt.

EXAMPLE 19

Catalyst: 1-methylborinatocobalt cycloocta-(1,5)-diene
0.088 g (0.3411 mmol) of 1-methylborinatocobalt cycloocta-(1,5)-diene is dissolved in 122.3 g (2.305 mol) of acrylonitrile. This solution is siphoned at 23° C. into a 500-ml stainless-steel autoclave with an interior cooling coil. The acrylonitrile is saturated at 16 bars with approximately 31 g (1.19 mol) of acetylene. The solution is heated for 11 minutes to 112° C. while the pressure in the autoclave is allowed to rise to a maximum of 35 bars at 90° C. The reaction is allowed to continue for 210 minutes, after which the autoclave is inwardly cooled with water to 20° C. in 8 minutes.

140.3 g of the crude product are withdrawn from the autoclave and the volatile components condensed off at 0.2 Torr, leaving a residue of 0.7 g.

Gas-chromatography shows that the 138.9 g of condensate contain 102.5 g (1.932 mol) of acrylonitrile and 29.3 g (0.279 mol) of 2-vinylpyridine, corresponding to a 21.1% solution of 2-vinylpyridine. The yield in terms of acrylonitrile converted is 74.8%. Catalyst utilization is 818 mol of 2-vinylpyridine/gram atom of cobalt.

EXAMPLE 20

Catalytic conversion of acetylene with cyanamide into 2-aminopyridine on 1-phenylborinatocobalt cycloocta-(1.5)-diene 0.0505 g (0.161 mmol) of 1-phenylborinatocobalt cycloocta-(1,5)-diene is dissolved in 128.7 g of N,N-dimethylformamide to which is added 14.3 g of monomeric cyanamide (97% of the product F 1000 manufactured by the firm of Süddeutsche Kalkstickstoff-Werke, 329.9 mmol). This reddish solution is siphoned at room temperature into a 500-ml stainless-steel autoclave with an interior cooling coil. The acrylonitrile is saturated at 12 bars with approximately 38.5 g (1.481 mol) of acetylene. The solution is heated for 15 minutes to 90° C. while the pressure in the autoclave is allowed to rise to a maximum of 29 bars. The reaction is allowed to continue for 120 minutes, after which the autoclave is inwardly cooled with water to 23° C. in 25 minutes.

145.6 g of the crude product are withdrawn from the autoclave and the volatile components distilled off in the vacuum.

| Fraction 1 | 30–32° C./4.5 Torr | 127.4 g |
| Fraction 2 | 60–78° C./4.5 Torr | 5.9 g |
| Residue | | 11.7 g |
| | | 145.0 g |

Gas-chromatography shows that Fraction 1 contains 485 mg (6.2 mmol) of benzene in addition to N,N-dimethylformamide.

Quantitative analysis shows that Fraction 2, a yellow liquid with a refractive index of $n_D^{20} = 1.5130$, consists of up to 91.2% 2-aminopyridine, corresponding to 5.381 g (57.2 mmol). The residue is mainly dimeric cyanamide.

Catalyst utilization is 355 mol of 2-aminopyridine/gram atom of cobalt or 566.5 kg of 2-aminopyridine/kg of cobalt.

What is claimed is:

1. A process for forming pyridine or pyridine substituted by alkyl, aryl, aralkyl or alkenyl which comprises contacting an alkyne with a cyano compound in the presence of a cobalt or rhodium catalyst which has one or two organo ligands with one or two boron atoms at $-10°$ to $+150°$ C. under pressure such that the reactants are at least partially in the liquid phase.

2. A process according to claim 1, wherein said cobalt or rhodium compound is complexly bounded with ligands forming penetration complexes having one or two boron atoms.

3. A process according to claim 1, wherein the catalyst is a bis-(borinato)cobalt complex of the formula $Co(C_5H_5BR)_2$ wherein R is methyl or phenyl.

4. A process according to claim 1, wherein said catalyst is a cobalt catalyst having at least one ligand with one or two boron atoms and said cobalt catalyst is a borinatocobalt diolefin complex of the formula Co(-diene)—$(C_5H_5BR)$ wherein R is phenyl or methyl.

5. A process according to claim 1, wherein said catalyst is phenyl borinatocobalt norbornadiene.

6. A process according to claim 1, wherein said catalyst is a substituted 1,3-diborolenylcobalt diolefin.

7. A process according to claim 1, wherein the cobalt or rhodium catalyst is one organo wherein the cobalt or rhodium-containing moiety is complexed with at least one ligand containing one or two boron atoms and the complex is formed in situ during synthesis of said pyridine or pyridine derivative.

8. A process according to claim 1 wherein the catalyst is (1,3,4,5-tetraethyl-2-methyl-1,3-diborolenyl)-cobalt(cycloocta-1,5-diene).

9. A process according to claim 1, wherein the catalyst is a borinatorhodium diolefin complex.

10. A process according to claim 1, wherein the catalyst is 1-phenylborinatocobalt cycloota-(1,5)-diene.

11. A process according to claim 1, wherein said catalyst is bis-1-phenylborinatocobalt.

12. A process according to claim 1 wherein said catalyst is methylheptadienylcobalt butadiene complexed with 1-phenyl-1,4-dihydroborabenzene.

13. A process according to claim 1, wherein the catalyst is (1,3,4,5-tetraethyl-2-methyl-1,3-diborolenyl)cobalt(cycloocta-1,5-diene).

14. A process according to claim 13, wherein said catalyst is formed in situ in the reaction mixture by contacting 1,3,4,5-tetraethyl-2-methyl-1,3-diborolene with π-cyclooctenylcobalt cycloocta-(1,5)-diene.

15. A process according to claim 1, wherein the catalyst is 1-phenylborinatorhodium cycloocta-(1,5)diene.

16. A process according to claim 1, wherein said catalyst is 1-methylborinatocobalt cycloocta-(1,5)diene.

17. A process according to claim 1, wherein said catalyst is a cobalt catalyst.

18. A process according to claim 1, wherein said catalyst is a rhodium catalyst.

19. A process according to claim 1, wherein said alkyne is acetylene.

20. A process according to claim 1, wherein said cyano compound is HCN.

21. A process according to claim 20, wherein said alkyne is acetylene.

22. A process according to claim 1, wherein said cyano compound is acrylonitrile.

23. A process according to claim 1, wherein said cyano compound is acetonitrile.

24. A process according to claim 1, wherein said cyano compound is propionitrile.

25. A process according to claim 1, wherein said alkine is propyne.

26. A process for preparing 2-aminopyridine, which comprises contacting cyanamide with acetylene in the presence of a cobalt or rhodium catalyst that has at least one ligand with one or two boron atoms.

27. A process according to claim 1, wherein the process is carried out at a temperature of 50° to 180° C.

28. A process according to claim 27, wherein the process is carried out at a pressure of 8 to 45 bars.

29. A process according to claim 1, wherein the process is carried out continuously.

30. A process according to claim 1 wherein the cyano compound is cyanamide.

31. A process according to claim 1 wherein said organo liquid is selected from the group consisting of a borabenzene compound, a borol, a borepine and an organo ligand having two boron atoms.

32. A process according to claim 31 wherein said organo liquid is a borabenzene ligand.

33. A process according to claim 31 wherein said organo ligand is a borol.

34. A process according to claim 31 wherein said organo boron ligand is a borepine.

35. A process according to claim 31 wherein said organo boron ligand is a ligand having two boron atoms.

36. A process according to claim 35 wherein said organo boron ligand is diborolene ligand.

* * * * *